United States Patent [19]
Gray

[11] Patent Number: 5,888,535
[45] Date of Patent: *Mar. 30, 1999

[54] METHODS AND COMPOSITIONS FOR TREATING GASTRIC DISORDERS USING OPTICALLY PURE (−) PANTOPRAZOLE

[75] Inventor: Nancy M. Gray, Marlboro, Mass.

[73] Assignee: Sepracor Inc., Marlborough, Mass.

[*] Notice: This patent issued on a continued prosecution application filed under 37 CFR 1.53(d), and is subject to the twenty year patent term provisions of 35 U.S.C. 154(a)(2).

[21] Appl. No.: 772,944

[22] Filed: Dec. 23, 1996

Related U.S. Application Data

[63] Continuation of Ser. No. 416,442, Apr. 3, 1995, abandoned, which is a continuation of Ser. No. 54,318, Apr. 27, 1993, abandoned.

[51] Int. Cl.$^6$ ..................................................... A61K 9/127
[52] U.S. Cl. .......................... 424/449; 424/451; 424/464; 514/338
[58] Field of Search .................................... 514/538, 338; 424/449, 451, 464

[56] References Cited

U.S. PATENT DOCUMENTS 4,758,579  7/1988  Kohl et al. .............................. 514/338

FOREIGN PATENT DOCUMENTS 4035455  5/1992  Germany .

OTHER PUBLICATIONS

Kromer et al J.Pharm. Exp. Ther. 254,129–135,1990.

*Primary Examiner*—Samuel Barts
*Attorney, Agent, or Firm*—Heslin & Rothenberg, P.C.

[57] ABSTRACT

Methods and compositions are disclosed utilizing optically pure (−) pantoprazole for the treatment of ulcers in humans while substantially reducing the concomitant liability of adverse effects associated with the racemic mixture of pantoprazole. The optically pure (−) isomer is also useful for the treatment of gastroesophageal reflux. (−) Pantoprazole is an inhibitor of H$^+$ release and is therefore useful in the treatment of other conditions related to gastric hypersecretion such as Zollinger-Ellison Syndrome.

28 Claims, No Drawings

METHODS AND COMPOSITIONS FOR TREATING GASTRIC DISORDERS USING OPTICALLY PURE (−) PANTOPRAZOLE

CROSS REFERENCE TO RELATED APPLICATIONS

This application is a continuation of earlier copending U.S. patent application Ser. No. 08/416,442 filed Apr. 3, 1995, which is itself a continuation of U.S. patent application Ser. No. 08/054,318 filed Apr. 27, 1993, both abandoned.

BACKGROUND OF THE INVENTION

This invention relates to novel compositions of matter containing optically pure (−) pantoprazole. These compositions possess potent activity in treating ulcers of the stomach, duodenum and esophagus, gastroesophageal reflux diseases, Zollinger-Ellison Syndrome, and other disorders including those that would benefit from an inhibitory action on gastric acid secretion. (−) Pantoprazole inhibits the $H^+$, $K^+$-ATPase associated with the gastric proton pump and the resulting secretion of gastric acid by parietal cells providing therapy in diseases associated with gastric hyperacidity. Optically pure (−) pantoprazole provides this treatment while substantially reducing adverse effects, including, but not limited to, hepatocellular neoplasia, gastrin hypersecretion, gastric neoplasms or carcinoids, headache, diarrhea and skin alterations which are associated with the administration of the racemic mixture of pantoprazole. Also disclosed are methods for treating the above described conditions in a human while substantially reducing the adverse effects that are associated with the racemic mixture of pantoprazole by administering the (−) isomer of pantoprazole to said human.

The active compound of these compositions and methods is an optical isomer of pantoprazole. The preparation of racemic pantoprazole is described in U.S. Pat. No. 4,758,579. The medicinal chemistry of pantoprazole is described by Kohl et al. [*J. Med. Chem.* 35, 1049–1057 (1992)], Kromer et al. [*J. Pharm. Exp. Ther.* 254, 129–135 (1990)], Simon et al. [*Aliment. Pharmacol. Therap.* 4, 239–245 (1990)], Beil et al. [*Europ. J. Pharmacol.* 218, 265–271 (1992)], and Kromer et al. [*Pharmacology* 41, 333–337 (1990)]. Chemically, the active compound is the (−) isomer of 5-(difluoromethoxy)-2-[[3,4-dimethoxy-2-pyridinyl)methyl]sulfinyl]-1H-benzimidazole(I), hereinafter referred to as pantoprazole.

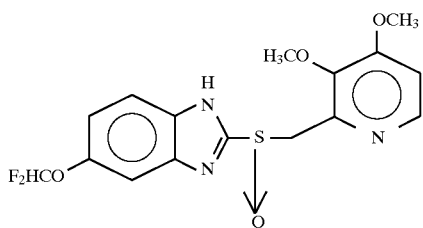

(−) Pantoprazole, which is the subject of the present invention, is not presently commercially available; only the 1:1 racemic mixture is commercially available as its sodium salt.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. There is no correlation between nomenclature for the absolute stereochemistry and for the rotation of an enantiomer. Thus, D-lactic acid is the same as (−) lactic acid, and L-lactic acid is (+). For a given chemical structure, these chiral compounds exist as a pair of enantiomers which are identical except that they are non-superimposable mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of the beta-adrenergic blocking agent, propranolol, which is known to be 100 times more potent than the D-enantiomer.

Furthermore, optical purity is important since certain isomers may actually be deleterious rather than simply inert. For example, it has been suggested that the D-enantiomer of thalidomide was a safe and effective sedative when prescribed for the control of morning sickness during pregnancy, while the corresponding L-enantiomer has been believed to be a potent teratogen.

The separation of racemic pantoprazole into (+) pantoprazole and (−) pantoprazole is described in German application 4,035,455, but no pharmacology of the individual enantiomers is reported.

Racemic pantoprazole had been in clinical trials in Europe and the United States under the sponsorship of two pharmaceutical manufacturers, but the United States and British sponsor withdrew in 1991 due to concerns about hepatocellular neoplasia seen in rats in a two year carcinogenicity study. Trials continue in Europe and initial reports indicate 90–100% ulcer healing in patients suffering from duodenal ulcers after four weeks of 20 to 80 mg of racemic pantoprazole per day.

Racemic pantoprazole sodium is an orally active, potent, irreversible inhibitor of $H^+$, $K^+$-ATPase. The compound is one of the class of compounds known as gastric "proton pump" inhibitors. These compounds are weak organic bases which diffuse passively from the plasma into the acid-containing intracellular canaliculi of gastric parietal cells. At the low pH found in the lumen of these canaliculi, the protonated compounds rearrange to form pyridinium sulfenamides, which react with sulfhydryl groups present on the ATPase localized in the membranes lining the intracellular canaliculi. The alkylation of the sulfhydryl inhibits the ability of the enzyme to catalyze the secretion of $H^+$into the lumen in exchange for $K^+$ions. This inhibition results in an overall reduction in hydrochloric acid secretion by the parietal cells into the cavity of the stomach, thus increasing intragastric pH. As a consequence of reduced acidity in the stomach, the activity of the proteolytic enzyme pepsin is also markedly decreased. Because the proton pump is the final step in acid production and the compounds of this class combine covalently with the associated $H^+$, $K^+$-ATPase, a profound and prolonged inhibition of gastric acid secretion can be achieved.

The potency of pantoprazole in vitro as an inhibitor of aminopyrine uptake, which is an index of acid secretion in isolated gastric glands, is similar to that of omeprazole, a structurally related antiulcer agent. Pantoprazole is, however, more chemically stable under neutral and moderately acidic conditions than is omeprazole. This may increase pantoprazole's selectivity for the acid secreting parietal cells, where low pH conditions exist in the intracellular canaliculi. In intact animals, pantoprazole is active in inhibiting gastric acid secretion in both rats and dogs. Specifically, the intravenous and oral doses required to reduce endogenous acid secretion in pylorus-ligated rats by 50% are in the 1–3 μmole/kg range. The calculated oral/intravenous (p.o./i.v.) ratio is approximately 2, suggesting good oral bioavailability. Racemic pantoprazole is also effective at doses less than 5 μmole/kg in inhibiting exogenously stimulated acid secretion induced by a variety of agonists, indicating general activity of the drug in inhibiting acid secretion. The serum half-life of racemic pantoprazole is 1.1 to 1.5 hours in humans. Compared to omeprazole, racemic pantoprazole is a weaker inhibitor of hepatic drug metabolizing enzyme systems in intact rats and rat microsomal enzyme preparations. The intravenous $LD_{50}$ values are 632 (rat) and 975 (mice) μmole/kg; oral $LD_{50}$ in mice is 1,893 and in rats >2,467 μmol/kg. The p.o./i.v. $LD_{50}$ ratio of the compound in mice is about 2 and the rat $LD_{50}$ values are at least two to three orders of magnitude greater than the corresponding doses required to produce half-maximal inhibition of endogenous acid secretion in this species.

Although no cardiovascular or obvious physical changes have been observed in humans on short-term administration of racemic pantoprazole, fasting serum gastrin levels are significantly elevated. This is cause for concern because prolonged elevated serum gastrin appears to be associated with diffuse and focal enterochromaffin-like cell hyperplasia and focal neoplasia (carcinoids) in rats. [Larsson et al. *Gastroenterology* 90, 391–399 (1986)]. Thus, despite its advantages, some adverse effects of racemic pantoprazole may remain, including, but not limited to, some incidence of hepatocellular neoplasia and gastric carcinoids on long-term therapy, and headache, diarrhea and skin alterations on acute therapy. It would therefore be particularly desirable to find a compound with the advantages of the racemic mixture of pantoprazole which would not have the aforementioned disadvantages.

SUMMARY OF THE INVENTION

It has now been discovered that the optically pure (−) isomer of pantoprazole is an effective agent for treating ulcers of the stomach, duodenum and esophagus, gastroesophageal reflux diseases, Zollinger-Ellison Syndrome and other disorders, including those that would benefit from an inhibitory action on $H^+$, $K^+$-ATPase. The optically pure (−) isomer of pantoprazole provides this effective treatment while substantially reducing the adverse effects of racemic pantoprazole including, but not limited to, hepatocellular neoplasia, gastric carcinoids, headache, diarrhea and skin alterations. The present invention also includes methods for treating the above described conditions in a human while substantially reducing the adverse effects that are associated with the racemic mixture of pantoprazole by administering the optically pure (−) isomer of pantoprazole to said human.

DETAILED DESCRIPTION OF THE INVENTION

The present invention encompasses a method of treating ulcers, which comprises administering to a human in need of such therapy, an amount of (−) pantoprazole, or a pharmaceutically acceptable salt thereof, substantially free of its (+) stereoisomer, said amount being sufficient to alleviate the symptoms of ulcers. The method substantially reduces the concomitant liability of adverse effects associated with the administration of the racemic compound by providing an amount which is insufficient to cause the adverse effects associated with the racemic mixture of pantoprazole.

The present invention also encompasses an antiulcer composition for the treatment of a human in need of antiulcer therapy, which comprises an amount of (−) pantoprazole, or a pharmaceutically acceptable salt thereof, substantially free of its (+) stereoisomer, said amount being sufficient to alleviate said ulcers. Preferably the amount is insufficient to cause the adverse effects associated with racemic pantoprazole.

The present invention further encompasses a method of treating gastroesophageal reflux disease in a human, which comprises administering to a human in need of such therapy, an amount of (−) pantoprazole, or a pharmaceutically acceptable salt thereof, substantially free of its (+) stereoisomer, sufficient to alleviate said gastroesophageal reflux. The method substantially reduces the concomitant liability of adverse effects associated with the administration of racemic pantoprazole by providing an amount which is insufficient to cause adverse effects associated with the administration of racemic pantoprazole.

In addition, the present invention encompasses a composition for the treatment of a human having gastroesophageal reflux disease, which comprises an amount of (−) pantoprazole, or a pharmaceutically acceptable salt thereof, substantially free of its (+) isomer, said amount being sufficient to alleviate or palliate said disorder. Preferably the amount is insufficient to cause adverse effects associated with the administration of racemic pantoprazole.

A further aspect of the present invention includes a method of treating a condition caused by or contributed to by gastric hypersecretion in a human, which comprises administering to a human in need of such therapy, an amount of (−) pantoprazole, or a pharmaceutically acceptable salt thereof, substantially free of its (+) stereoisomer, sufficient to alleviate said gastric hypersecretion. The method substantially reduces the concomitant liability of adverse effects associated with the administration of racemic pantoprazole by providing an amount which is insufficient to cause adverse effects associated with the administration of racemic pantoprazole. Conditions associated with hypersecretion in humans may include, but are not limited to, Zollinger-Ellison syndrome.

In addition, the invention encompasses a composition for the treatment of a condition caused by or contributed to by gastric hypersecretion in a human which comprises an amount of (−) pantoprazole or a pharmaceutically acceptable salt thereof, substantially free of its (+) stereoisomer, the amount being sufficient to alleviate the condition. Preferably the amount is insufficient to cause adverse effects associated with the administration of racemic pantoprazole.

The available racemic mixture of pantoprazole (i.e., a 1:1 racemic mixture of the two enantiomers) exhibits antiulcer activity through its selective, potent, and irreversible inhibition of $H^+$, $K^+$-ATPase, thus providing therapy and a reduction of symptoms in a variety of conditions and disorders related to hypersecretion; however, this racemic mixture, while offering the expectation of efficacy, causes adverse effects which are serious enough to have caused curtailment of clinical trials. Utilizing the optically pure or substantially optically pure isomer of (−) pantoprazole results in enhanced efficacy, diminished adverse effects, and accordingly, an improved therapeutic index. It is therefore, more desirable to use the (−) isomer of pantoprazole than to administer the racemic mixture.

The term "adverse effects" includes, but is not limited to, hepatocellular neoplasia, gastrin hypersecretion, gastric carcinoids, headache, diarrhea and skin alterations.

The term "substantially free of its (+) stereoisomer" as used herein means that the compositions contain at least 90% by weight of (−) pantoprazole and 10% by weight or less of (+) pantoprazole. In a more preferred embodiment the term "substantially free of the (+) isomer" means that the composition contains at least 99% by weight of (−) pantoprazole, and 1% or less of (+) pantoprazole. In the most preferred embodiment, the term "substantially free of its (+) stereoisomer" as used herein means that the composition contains greater than 99% by weight of (−) pantoprazole. These percentages are based upon the total amount of pantoprazole in the composition. The terms "substantially optically pure (−) isomer of pantoprazole" or "substantially optically pure (−) pantoprazole" and "optically pure (−) isomer of pantoprazole" and "optically pure (−) pantoprazole" are also encompassed by the above-described amounts.

The term "treating ulcers" as used herein means treating, alleviating or palliating such conditions, and thus providing relief from the symptoms of nausea, heartburn, post-prandial pain, vomiting, and diarrhea.

The term "a method for treating gastroesophageal reflux diseases in a human" as used herein means treating, alleviating or palliating the conditions that result from the backward flow of the stomach contents into the esophagus.

The term "treating a condition caused, or contributed to, by gastric hypersecretion in a human" as used herein means treating, alleviating or palliating such disorders associated with hypersecretion, thus providing relief from the symptoms of the aforementioned conditions. Zollinger-Ellison Syndrome is among the conditions caused by or contributed to by hypersecretion.

The chemical synthesis of the racemic mixture of pantoprazole can be performed by the method described in U.S. Pat. No. 4,758,579 cited above. The (−) isomer of pantoprazole may then be obtained from its racemic mixture by resolution of the enantiomers of pantoprazole or precursors thereto using conventional means such as an optically active resolving base. German application 4,035,455 (Kohl et al.), which is incorporated herein by reference, discloses a method for resolving the racemic pantoprazole by forming an alkoxymethylamine with fenchyl chloromethyl ether. Other standard methods of resolution known to those skilled in the art including, but not limited to, simple crystallization and chromatographic resolution, can also be used. (See for example, E. L. Eliel, *Stereochemistry of Carbon Compounds*, McGraw Hill (1962) and [Wilen and Lochmuller "Tables of Resolving Agents" *Journal of Chromatography* 113, 283–302 (1975)]. Alternatively, the prochiral sulfide may be enantiospecifically oxidized to the (−) sulfoxide by processes known in the art.

The magnitude of a prophylactic or therapeutic dose of (−) pantoprazole in the acute or chronic management of disease will vary with the severity of the condition to be treated and the route of administration. The dose and perhaps the dose frequency will also vary according to the age, body weight and response of the individual patient. In general, the total daily dose range for (−) pantoprazole for the conditions described herein is from about 5.0 mg to about 125 mg in single or divided doses. Preferably a daily dose range should be about 10 mg to about 100 mg in single or divided doses while most preferably a daily dose range should be about 20 mg to about 80 mg in single or divided doses. In managing the patient, the therapy should be initiated at a lower dose, perhaps at about 10 mg to about 25 mg and increased up to about 80 mg or higher depending on the patient's global response. It is further recommended that children and patients over 65 years and those with impaired renal or hepatic function, initially receive low doses, and that they be titrated based on individual response(s) and blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response. The terms "an amount sufficient to alleviate or palliate ulcers but insufficient to cause said adverse effects," "an amount sufficient to alleviate the symptoms of gastroesophageal reflux but insufficient to cause said adverse effects," and "an amount sufficient to alleviate gastric hypersecretion but insufficient to cause said adverse effects" are encompassed by the above-described dosage amounts and dose frequency schedule.

Any suitable route of administration may be employed for providing the patient with an effective dosage of (−) pantoprazole. For example, oral, rectal, parenteral (subcutaneous, intramuscular, intravenous), transdermal, and like forms of administration may be employed. Dosage forms include tablets, troches, dispersions, suspensions, solutions, capsules, patches, and the like.

The pharmaceutical compositions of the present invention comprise (−) pantoprazole as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic bases. Since the compound of the present invention is a weak acid ($pK_a$=8.2), salts may be prepared from pharmaceutically acceptable non-toxic bases including inorganic and organic bases. Suitable pharmaceutically acceptable base addition salts for the compound of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Sodium salts are particularly preferred.

The compositions of the present invention include suspensions, solutions, elixirs, aerosols, or solid dosage forms. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations.

Because of their ease of administration, tablets and capsules represent the most advantageous oral dosage unit forms, in which case solid pharmaceutical carriers are employed. If desired, tablets may be coated by standard aqueous or nonaqueous techniques.

In addition to the common dosage forms set out above, the compounds of the present invention may also be administered by controlled release means and delivery devices such as those described in U.S. Pat. Nos.: 3,845,770; 3,916,899; 3,536,809; 3,598,123; and 4,008,719, the disclosures of which are hereby incorporated by reference.

Pharmaceutical compositions of the present invention suitable for oral administration may be presented as discrete units such as capsules, cachets, tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding in a suitable machine, a mixture of the powdered compound-moistened with an inert liquid diluent. Desirably, each tablet contains from about 10 mg to about 100 mg of the active ingredient, and each cachet or capsule contains from about 10 mg to about 100 mg of the active ingredient. Most preferably, the tablet, cachet or capsule contains either one of three dosages, about 20 mg, about 40 mg or about 80 mg of (−) pantoprazole sodium salt for oral administration.

The invention is further defined by reference to the following examples describing in detail the preparation of the compositions of the present invention, as well as their utility. It will be apparent to those skilled in the art that many modifications, both to materials and methods, may be practiced without departing from the purpose and interest of this invention.

EXAMPLES

Example 1

The relative activity, potency and specificity of optically pure pantoprazole and racemic pantoprazole both as gastric antisecretory agents and plasma gastrin elevating agents can be determined by a pharmacological study in animals according to the method of Decktor et al. [*J. Pharmacol. Exp. Ther.* 249, 1–5 (1989)]. The test provides an estimate of relative activity, potency and, through a measure of specificity, an estimate of therapeutic index. Fasted rats, implanted with a gastric cannula, receive single oral or parenteral doses of (−) pantoprazole, (+) pantoprazole or racemate, 1 hour before collection of gastric juice over a four hour period. Acid output and pH are then determined on each sample. Dose response evaluations are performed with each compound to determine the lowest dose which inhibits acid output by at least 95% and maintains gastric pH above 7.0. Plasma gastrin levels are then determined in a second group of rats treated with the doses selected in the first series of tests. Blood samples are taken for analyses over the five hour period after dosing, and both peak level as well as area-under-the-curve analyses of the gastrin responses are made. These responses are then analyzed statistically using Student's "t" test to assess whether equivalent antisecretory doses show differences in gastrin responses.

Example 2

ORAL FORMULATION
Capsules:

| Formula | Quantity per capsule in mg | | |
|---|---|---|---|
| | A | B | C |
| (−) Pantoprazole sodium salt | 20 | 40 | 80 |
| Lactose | 152 | 132 | 142 |
| Cornstarch | 27.5 | 27.5 | 27.5 |
| Magnesium Stearate | 0.50 | 0.50 | 0.50 |
| Compression Weight | 200 | 200 | 250 |

The (−) pantoprazole, lactose and cornstarch are blended until uniform and then the magnesium stearate is blended into the resulting powder, which is sieved and filled into suitably sized, two-piece, hard gelatin capsules using conventional machinery. Other doses may be prepared by altering the fill weight and, if necessary, changing the capsule size to suit.

Example 3

ORAL FORMULATION
Tablets:

| Formula | Quantity per tablet in mg | | |
|---|---|---|---|
| | A | B | C |
| (−) Pantoprazole sodium salt | 20 | 40 | 80 |
| Lactose | 147 | 127 | 137 |
| Cornstarch | 5 | 5 | 5 |
| Water (per thousand Tablets)* | 48 mL | 48 mL | 48 mL |
| Cornstarch | 27.5 | 27.5 | 27.5 |
| Magnesium Stearate | 0.50 | 0.50 | 0.50 |
| Compression Weight | 200 | 200 | 250 |

*The water evaporates during manufacture

The (−) pantoprazole is blended with the lactose until a uniform blend is formed. The smaller quantity of cornstarch is blended with the water to form the resulting corn starch paste. This is then mixed with the uniform blend until a uniform wet mass is formed. The remaining cornstarch is added to the resulting wet mass and mixed until uniform granules are obtained. The granules are then screened through a suitable milling machine, using a ¼ inch stainless steel screen. The milled granules are dried in a suitable drying oven until the desired moisture content is obtained. The dried granules are then milled through a suitable milling machine, magnesium stearate is blended in, and the resulting mixture is compressed into tablets of the desired shape, thickness, hardness and disintegration. Tablets of other strengths may be prepared by altering the ratio of active ingredient to the excipients or to the final weight of the tablet. An enteric coating, such as the polyacrylate Eudragit L® and Eudragit S® series, is applied by spray coating the tablets, preferably with an aqueous dispersion of the coating polymer.

What is claimed is:

1. A method of treating ulcers in a human which comprises administering to said human an amount of (−) pantoprazole, or a pharmaceutically acceptable salt thereof, substantially free of its (+) stereoisomer, said amount being sufficient to alleviate or palliate said ulcers.

2. The method of claim 1 wherein (−) pantoprazole is administered parenterally, transdermally, or orally as a tablet or a capsule.

3. The method of claim 2 wherein the amount of (−) pantoprazole or a pharmaceutically acceptable salt thereof administered is from about 5 mg to about 125 mg per day.

4. The method of claim 3 wherein the amount administered is from. about 10 mg to about 100 mg per day.

5. The method of claim 4 wherein the amount administered is from about 20 mg to about 80 mg per day.

6. The method of claim 1 wherein the amount of (−) pantoprazole or a pharmaceutically acceptable salt thereof is greater than approximately 90% by weight of the total weight of pantoprazole.

7. The method of claim 1 wherein the amount of said (−) pantoprazole or a pharmaceutically acceptable salt thereof, substantially free of its (+) stereoisomer, is administered together with a pharmaceutically acceptable carrier.

8. The method according to claim 1, wherein (−) pantoprazole is administered as a sodium salt.

9. A method of treating ulcers in a human while substantially reducing the concomitant liability of adverse effects associated with racemic pantoprazole which comprises administering to a human in need of such antiulcer therapy an amount of (−) pantoprazole, or a pharmaceutically acceptable salt thereof, substantially free of its (+) stereoisomer, said amount being sufficient to alleviate or palliate said ulcers but insufficient to cause said adverse effects.

10. A method of treating gastroesophageal reflux disease in a human which comprises administering to said human an amount of (−) pantoprazole, or a pharmaceutically acceptable salt thereof, substantially free of its (+) stereoisomer, said amount being sufficient to alleviate symptoms of gastroesophageal reflux.

11. The method of claim 10 wherein (−) pantoprazole is administered parenterally, transdermally, or orally as a tablet or a capsule.

12. The method of claim 11 wherein the amount of (−) pantoprazole or a pharmaceutically acceptable salt thereof administered is from about 5 mg to about 125 mg per day.

13. The method of claim 12 wherein the amount administered is from about 10 mg to about 100 mg per day.

14. The method of claim 13 wherein the amount administered is from about 20 mg to about 80 mg per day.

15. The method of claim 10 wherein the amount of (−) pantoprazole or a pharmaceutically acceptable salt thereof is greater than approximately 90% by weight of the total weight of pantoprazole.

16. The method of claim 10 wherein the amount of said (−) pantoprazole or a pharmaceutically acceptable salt thereof, substantially free of its (+) stereoisomer, is administered together with a pharmaceutically acceptable carrier.

17. The method according to claim 10, wherein (−) pantoprazole is administered as a sodium salt.

18. A method of treating gastroesophageal reflux disease in a human, while substantially reducing the concomitant liability of adverse effects associated with racemic pantoprazole, which comprises administering to a human in need of such therapy an amount of (−) pantoprazole, or a pharmaceutically acceptable salt thereof, substantially free of its (+) stereoisomer, said amount being sufficient to alleviate symptoms of gastroesophageal reflux but insufficient to cause said adverse effects.

19. A method of treating a condition caused by or contributed to by gastric hypersecretion in a human which comprises administering to said human an amount of (−) pantoprazole, or a pharmaceutically acceptable salt thereof, substantially free of its (+) stereoisomer, said amount being sufficient to alleviate said gastric hypersecretion.

20. The method according to claim 19 wherein said condition is zollinger-Ellison Syndrome.

21. The method of claim 19 wherein (−) pantoprazole is administered parenterally, transdermally, or orally as a tablet or a capsule.

22. The method of claim 21 wherein the amount of (−) pantoprazole or a pharmaceutically acceptable salt thereof administered is from about 5 mg to about 125 mg per day.

23. The method of claim 22 wherein the amount administered is from about 10 mg to about 100 mg per day.

24. The method of claim 23 wherein the amount administered is from about 20 mg to about 80 mg per day.

25. The method of claim 19 wherein the amount of (−) pantoprazole or a pharmaceutically acceptable salt thereof is greater than approximately 90% by weight of the total weight of pantoprazole.

26. The method of claim 19 wherein the amount of said (−) pantoprazole or a pharmaceutically acceptable salt thereof, substantially free of its (+) stereoisomer, is administered together with a pharmaceutically acceptable carrier.

27. The method according to claim 19, wherein (−) pantoprazole is administered as a sodium salt.

28. A method of treating a condition caused by or contributed to by gastric hypersecretion in a human, while substantially reducing the concomitant liability of adverse effects associated with racemic pantoprazole, which comprises administering to a human, in need of such therapy, an amount of (−) pantoprazole, or a pharmaceutically acceptable salt thereof, substantially free of its (+) stereoisomer, said amount being sufficient to alleviate said gastric hypersecretion but insufficient to cause said adverse effects.

* * * * *